US00PP08929P

United States Patent [19]

van Diemen

[11] Patent Number: Plant 8,929

[45] Date of Patent: Oct. 4, 1994

[54] *FICUS BENJAMINA* PLANT NAMED RIANNE

[75] Inventor: Hubertus T. van Diemen, Aalsmeer, Netherlands

[73] Assignee: Kwekerij De Amstel, B.V., Netherlands

[21] Appl. No.: 165,242

[22] Filed: Dec. 10, 1993

[51] Int. Cl.[5] ..... A01H 5/00

[52] U.S. Cl. ..... Plt./88.9

[58] Field of Search ..... Plt. 88.9

*Primary Examiner*—James R. Feyrer

*Attorney, Agent, or Firm*—Christie, Parker & Hale

[57] ABSTRACT

A *Ficus benjamina* plant having a laterally dominant growth habit.

1 Drawing Sheet

BACKGROUND OF THE INVENTION

The present invention comprises a new and distinct cultivar of *Ficus benjamina*. The varietal denomination of the new cultivar is 'Rianne.'

The new variety was discovered as a mutation in a controlled planting of *Ficus benjamina* Exotica in a greenhouse in Aalsmeer, The Netherlands.

SUMMARY OF THE INVENTION

The new variety is a mutation of the variety *Ficus benjamin* Exotica and differs significantly in growth habit and appearance from its parent. Whereas *Ficus benjamina* exhibits a vertical, upright growth pattern, 'Rianne' has a substantially horizontal, or laterally dominant habit of growth. Although growth of the new variety will eventually progress vertically, it does so much slower than its parent. For example, where its parent takes six months for a vegetative cutting of 8 cm to reach one meter in height, 'Rianne' takes two years. In addition, the growth form of 'Rianne' exhibits a zig-zag uneven branching, sometimes branching at about right angles, whereas the parent exhibits a dominant vertical growth pattern with upright multiple branching. The leaves of the new variety tend to be slightly smaller than the parent, and with alternate ovate-elliptical and acuminate leaf tip. The growth habit of 'Rianne' makes it suitable for varied uses, including growing in containers.

The new variety has been asexually reproduced vegetatively by rooted cuttings in Aalsmeer, The Netherlands. Asexual reproduction through succeeding generations has established that the combination of characteristics as herein disclosed for the new cultivar is firmly fixed and is retained through successive generations of asexual reproduction.

BRIEF DESCRIPTION OF THE ILLUSTRATION

The accompanying illustration shows a specimen of the new cultivar in a photo illustration as true to color as is reasonably possible to make in an illustration of this character, and describes the laterally dominant growth habit.

DESCRIPTION OF THE NEW VARIETY

'Rianne' has not been observed under all possible environmental conditions. The phenotypic expression may vary with variations in environment such as temperature, light intensity and day length. The following observations and descriptions are of plants grown in Aalsmeer, the Netherlands, in a greenhouse. In this description, color references are to The Royal Horticultural Society Colour Chart (R.H.S.C.C.). The terminology used in the color descriptions herein refers to plate numbers in this color chart.

Classification:

*Botanical.*—*Ficus benjamina* cv. 'Rianne'.

Percentage: Mutation of *Ficus benjamina* Exotica.

Propagation: By vegetative cuttings and other known asexual reproduction techniques.

PLANT

A. Form: Multiple lateral branching woody ornamental.

B. Growth: Vigorous, multiple irregular zig-zag branching.

*Height attained.*—About one meter after two years.

C. Foliage:

1. *Size.*—About 2.8 cm wide by about 7.5 cm long (to leaf tip). Young leaf tips curl downward.
2. *Quantity.*—Multiple, numerous.
3. *Color.*—New foliage: Upper side — near 144A. Old foliage: Upper side —near 139A.
4. *Shape.*—Ovate elliptical — acuminate leaf tip.
5. *Texture.*—Leathery, glossy.
6. *Veination.*—Insignificant, 1 mm or less.
7. *Edge.*—Smooth.
8. *Serration.*—None.
9. *Stipules.*—Leaves are glossy and leathery.
10. *Auricle.*—Absent.
11. *Petiole.*—Near 199A; about 15 mm.
12. *To disease.*—Resistant to anthracnose, *Agrobacterium radiobacter*, tumefaciens, *Heterodera fici.*
13. *Rachis.*—None.

D. Wood:

*New shoots.*—Color — near 148A.

*Old wood.*—Color — near 199A.

Note: To date, and under conditions described herein, the new variety has not borne flowers or fruit.

Temperature range: To 0° C., will resist to −1° C.

Internode spacing: Variable, irregular, between about 2 cm – 3 cm.

Preferred growing conditions: 20° C. to 30° C.

Growth habit: Multiple branching, wood ornamental.

Leaves per stem: Multiple, alternative, irregular.

I claim:

1. A new and distinct cultivar of *Ficus benjamina* named 'Rianne', substantially as illustrated and described, particularly characterized by a plant with laterally dominant growth habit.

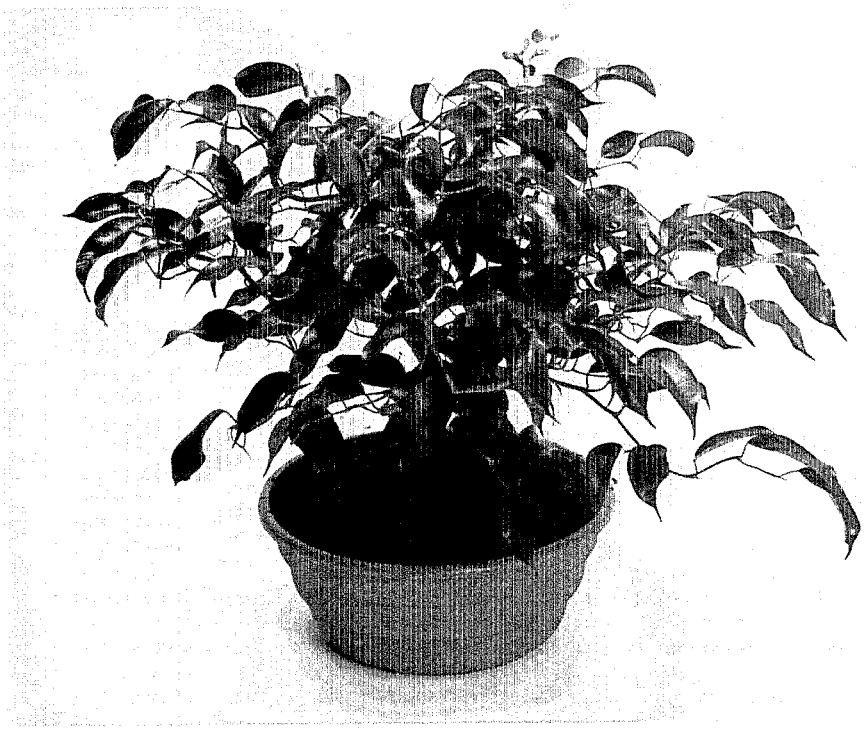

* * * * *